US011456069B2

United States Patent
Park et al.

(10) Patent No.: US 11,456,069 B2
(45) Date of Patent: Sep. 27, 2022

(54) SYSTEM AND METHOD FOR PROVIDING CUSTOMIZED TREATMENT INFORMATION FOR BEHAVIORAL CONTROL OF DENTAL PATIENTS

(71) Applicant: Kaii Company Inc., Daejeon (KR)

(72) Inventors: Sung-Hae Park, Daejeon (KR); Ji-Hyang Bak, Gimhae-si (KR); Ho-Chung Chung, Daejeon (KR)

(73) Assignee: Kaii Company Inc., Daejeon (KR)

( * ) Notice: Subject to any disclaimer, the term of this patent is extended or adjusted under 35 U.S.C. 154(b) by 739 days.

(21) Appl. No.: 15/755,060

(22) PCT Filed: Jul. 6, 2016

(86) PCT No.: PCT/KR2016/007276
§ 371 (c)(1),
(2) Date: Feb. 23, 2018

(87) PCT Pub. No.: WO2017/034149
PCT Pub. Date: Mar. 2, 2017

(65) Prior Publication Data
US 2018/0197630 A1 Jul. 12, 2018

(30) Foreign Application Priority Data

Aug. 26, 2015 (KR) .................. 10-2015-0120210

(51) Int. Cl.
*G16H 20/70* (2018.01)
*G16H 20/40* (2018.01)
(Continued)

(52) U.S. Cl.
CPC .............. *G16H 20/70* (2018.01); *G06Q 10/10* (2013.01); *G16H 10/60* (2018.01); *G16H 20/40* (2018.01); *G16H 40/20* (2018.01)

(58) Field of Classification Search
CPC ........ G16H 20/40; G16H 20/70; G16H 40/20; G16H 10/60; G06F 19/30; G06F 19/32;
(Continued)

(56) References Cited

U.S. PATENT DOCUMENTS

2011/0258570 A1\* 10/2011 Bucolo .................. G06Q 10/10
715/771
2013/0040272 A1\* 2/2013 Booher .................. G16H 20/30
434/254
(Continued)

FOREIGN PATENT DOCUMENTS

JP     2005-514122 A     5/2005
JP     2011-528126 A     11/2011
(Continued)

OTHER PUBLICATIONS

PCT International Search Report; PCT/KR2016/007276; dated Nov. 9, 2016.

*Primary Examiner* — John P Go
*Assistant Examiner* — Christopher B Wehrly
(74) *Attorney, Agent, or Firm* — Pramudji Law Group PLLC; Ari Pramudji

(57) ABSTRACT

A system for providing customized treatment information for behavioral control of dental patients. The system may include a management server, a hospital server, a waiting room terminal, a terminal determination unit, and a treatment room server. The management server may include an arithmetic process unit and a management server extraction unit. The hospital server may include a hospital server transmission/reception unit. The waiting room terminal may include a terminal extraction unit, a terminal output unit, and a terminal determination unit. The treatment room server (Continued)

may include a treatment server extraction unit, a treatment room server output unit, and a treatment room server determination unit.

17 Claims, 6 Drawing Sheets

(51) Int. Cl.
  *G16H 40/20* (2018.01)
  *G06Q 10/10* (2012.01)
  *G16H 10/60* (2018.01)
(58) Field of Classification Search
  CPC .... G06F 19/328; G06F 19/34; G06F 19/3456; G06F 19/3462; G06F 19/3468; G06F 19/3475; G06F 19/3481; G06Q 50/22; G06Q 50/24
  USPC .......................................................... 705/2, 3
  See application file for complete search history.

(56) References Cited

U.S. PATENT DOCUMENTS

| 2015/0012289 A1* | 1/2015 | Ben | G16H 10/60 |
| | | | 705/2 |
| 2015/0287330 A1* | 10/2015 | Kron | G09B 23/28 |
| | | | 434/219 |
| 2015/0306340 A1* | 10/2015 | Giap | A61B 6/461 |
| | | | 600/301 |
| 2016/0147951 A1* | 5/2016 | Francois | G16H 20/30 |
| | | | 705/3 |
| 2017/0100207 A1* | 4/2017 | Wen | G06T 11/60 |

FOREIGN PATENT DOCUMENTS

| JP | 2007-068816 A | 3/2017 |
| KR | 10-2013-0076493 A | 7/2013 |
| KR | 10-2014-0060918 A | 5/2014 |

* cited by examiner

[Figure 1]
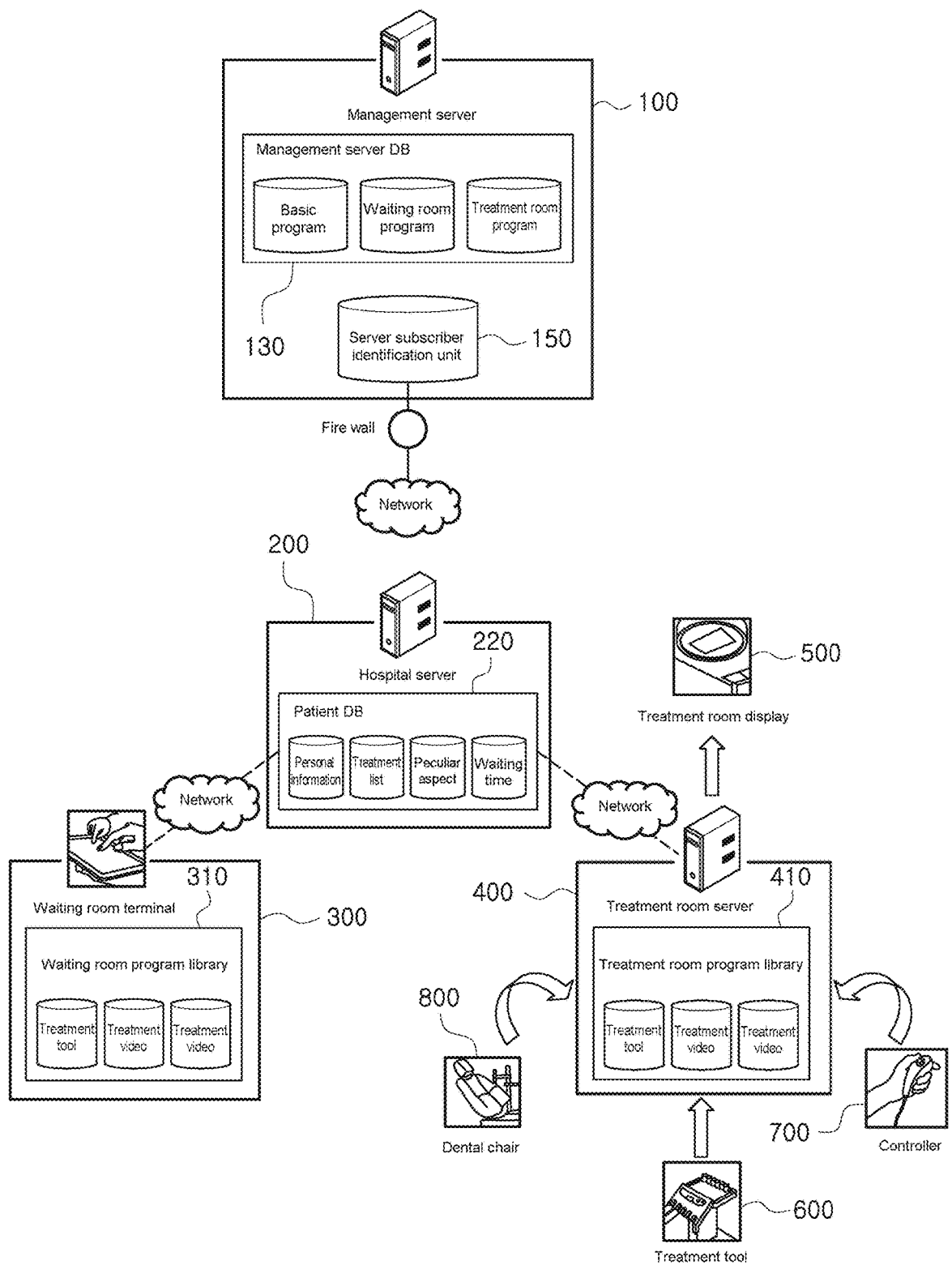

[Figure 2]
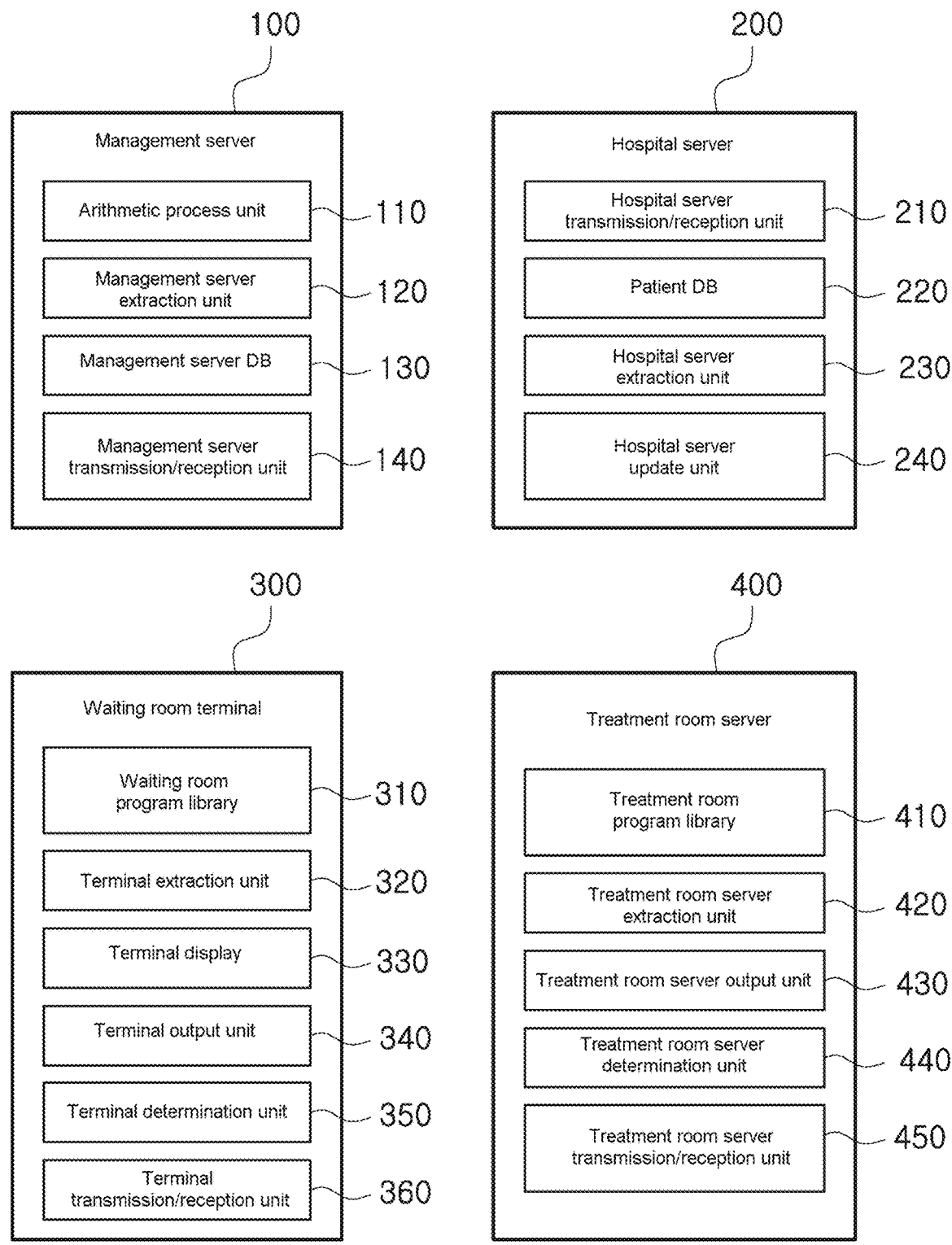

[Figure 3]
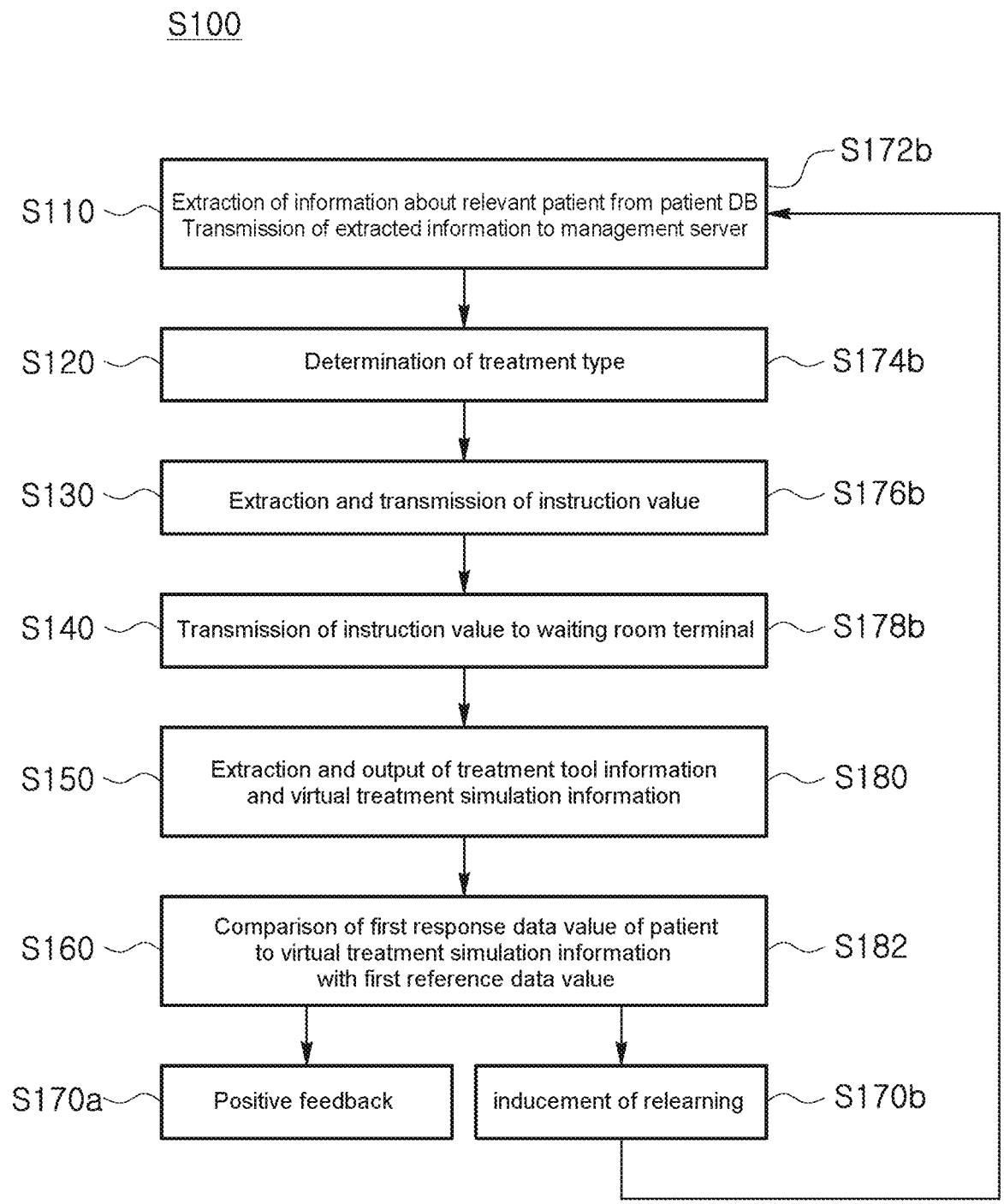

[Figure 4]
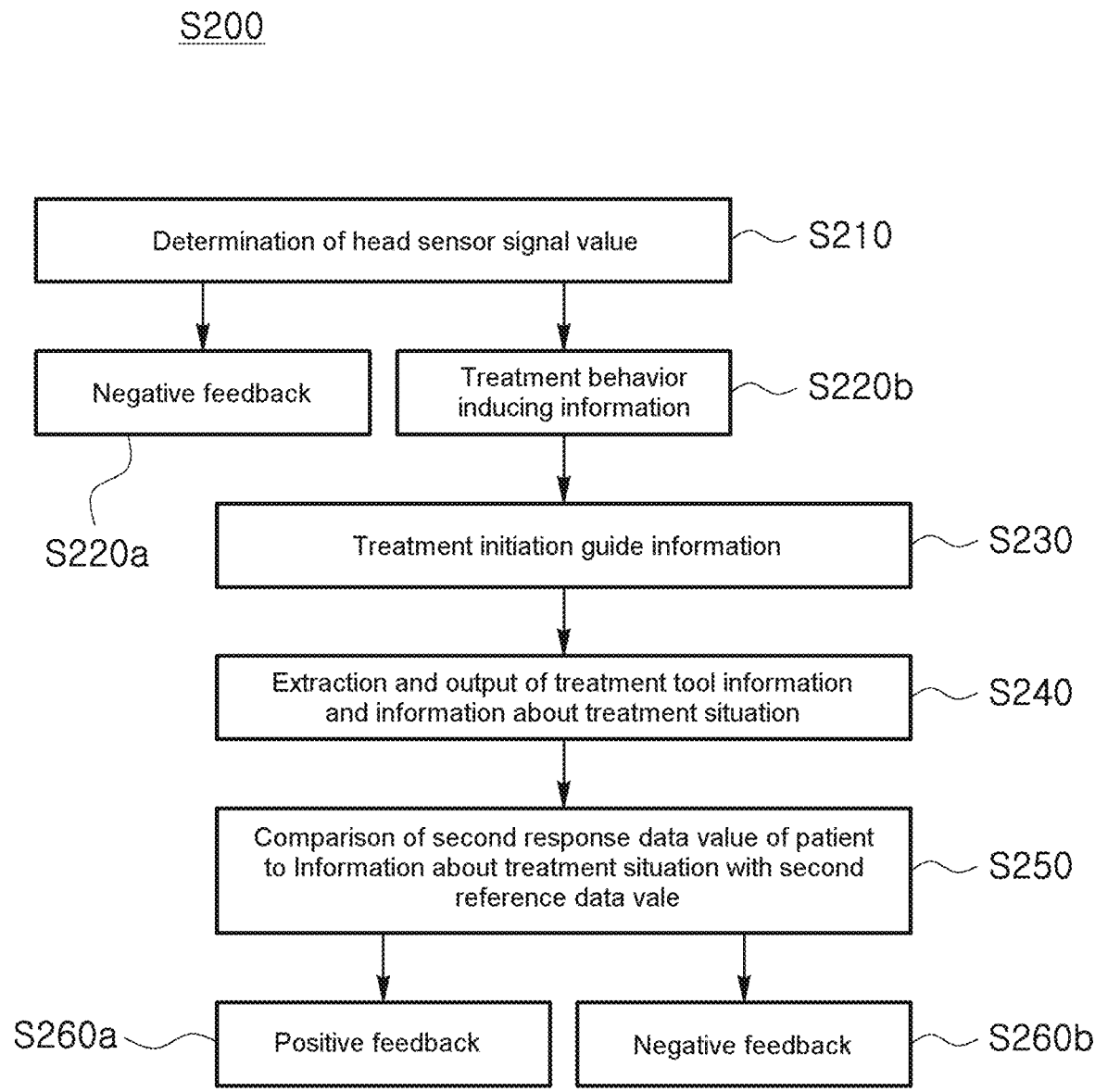

[Figure 5]
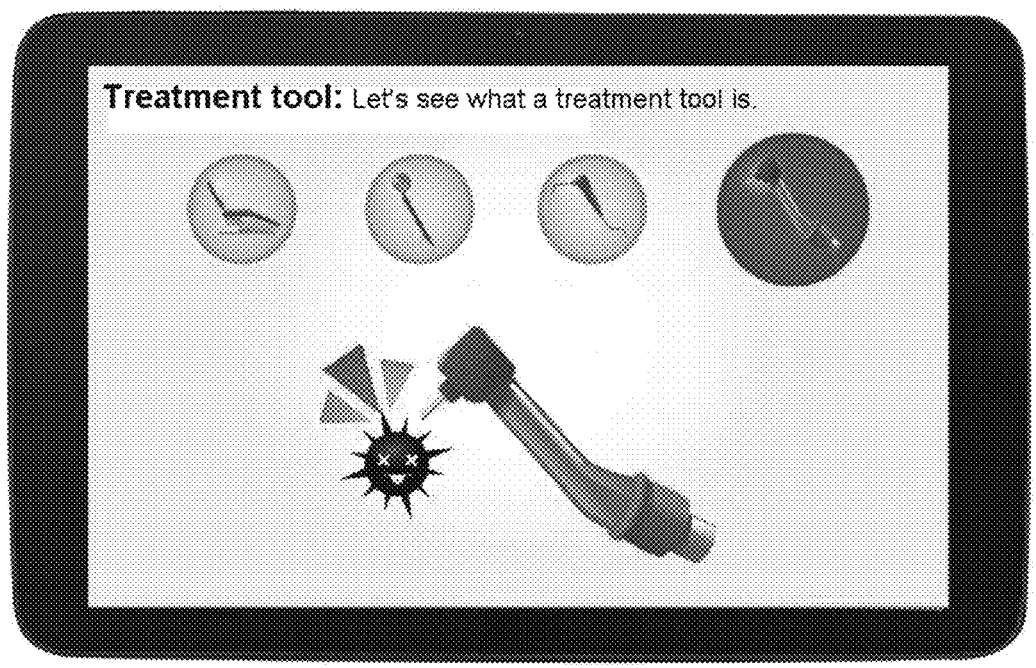
[Figure 6]
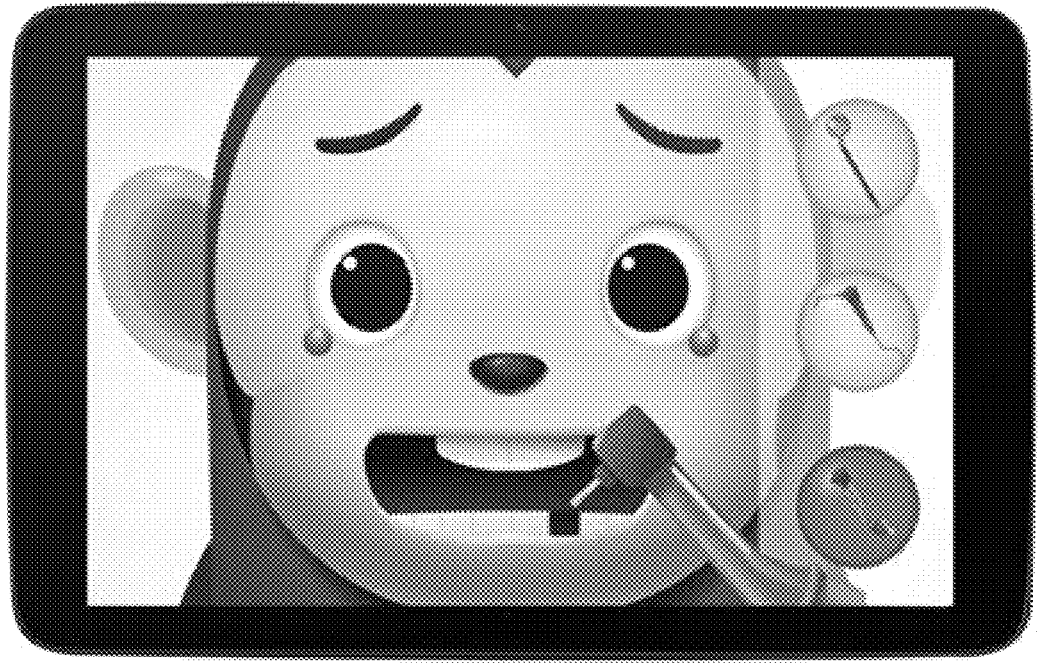

[Figure 7]
[Figure 8]
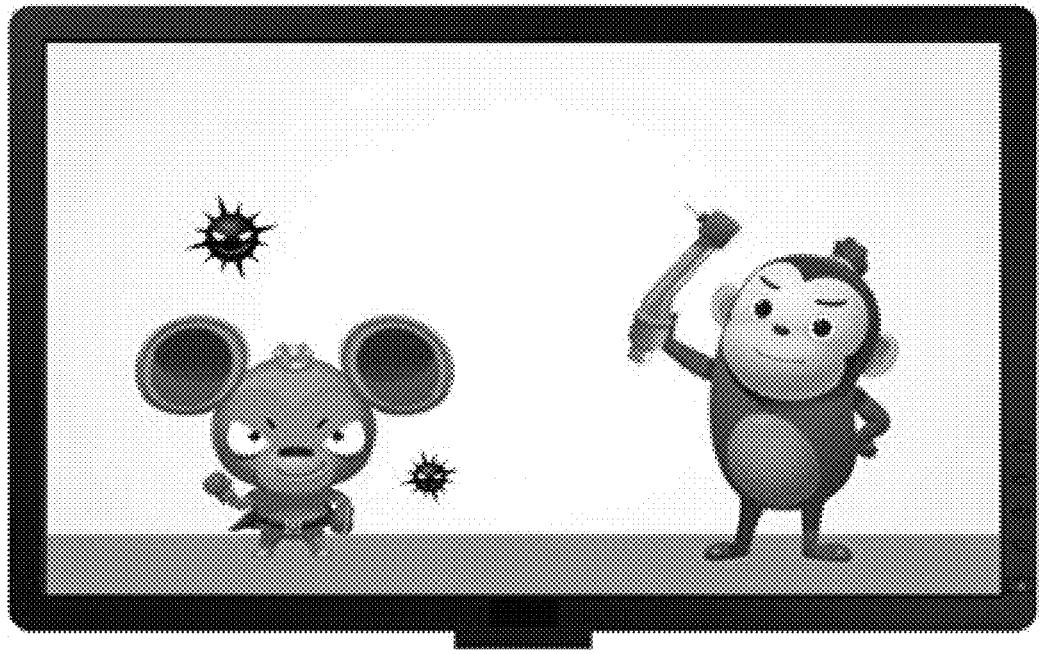

SYSTEM AND METHOD FOR PROVIDING CUSTOMIZED TREATMENT INFORMATION FOR BEHAVIORAL CONTROL OF DENTAL PATIENTS

TECHNICAL FIELD

The present invention relates to a system and method for providing customized treatment information for behavioral control of dental patients. More specifically, the invention relates to a system and method for providing customized treatment information for behavioral control of dental patients, which provides various pieces of dental treatment information which is animated by using characters and which is appropriate for a treatment type and treatment behavior of relevant patient, thereby increasing positive understanding of and motivation for treatment.

BACKGROUND ART

At the dentist, the cavity treatment, extraction and teeth scaling etc. are the main treatments.

However, when a pediatric patient gets such a treatment, it is difficult to create a situation to receive appropriate treatment. This is because the patient refuses treatment due to vague sense of anxiety and pain associated with treatment, or even if receiving treatment the patient moves his or her body or cries during the treatment.

SUMMARY OF INVENTION

Technical Problem

The invention has been devised to solve a problem as stated above. The object of the invention is to provide a system and method for providing customized treatment information for behavioral control of dental patients, allowing patients, particularly pediatric patients to actively participate in treatment without anxiety and receive treatment smoothly.

Solution to Problem

To achieve the foregoing object, a system for providing customized treatment information for behavioral control of dental patients in accordance with the present invention comprises: a management server comprising a management server arithmetic process unit which determines a treatment type of a patient based on information in a patient DB, and a management server extraction unit which extracts an instruction value according to the determined treatment type from a management server DB; a hospital server comprising a hospital server transmission/reception unit which receives the extracted instruction value from the management server; a waiting room terminal; and a treatment room server, wherein the waiting room terminal comprises: a terminal extraction unit extracting treatment tool information and virtual treatment simulation information from a waiting room program library based on the instruction value received from the hospital server; a terminal output unit outputting the extracted treatment tool information and virtual treatment simulation information on a terminal display; and a terminal determination unit comparing a first response data value of the patient to the virtual treatment simulation information with a first reference data value and determining whether to give positive feedback or induce relearning, wherein the treatment room server comprises: a treatment room server extraction unit extracting, based on a signal value from a contact sensor of a treatment tool, relevant treatment tool information and information about a treatment situation in which the treatment tool is used, from a treatment room program library; a treatment room server output unit outputting the extracted relevant treatment tool information and information about a treatment situation in which the treatment tool is used, on a treatment room display; and a treatment room server determination unit comparing a second response data value of the patient to the information about a treatment situation with a second reference data value and determining whether to give positive feedback or give negative feedback.

Preferably, the patient DB comprises: a personal information DB comprising names, sexes, and ages; a treatment list DB comprising diagnosis information and teeth positional information; a peculiar aspect DB comprising a treatment compliance level; and a waiting time DB comprising a patient who is waiting, a patient whose medical treatment has been initiated, and a patient whose medical treatment has been finished, and estimated time of waiting.

The treatment type of a patient is determined based on diagnosis information, teeth positional information, and a treatment compliance level.

If it is determined to give positive feedback since the first response data value is less than or equal to the first reference data value, the terminal extraction unit extracts positive feedback from the waiting room program library, and the terminal output unit outputs the extracted positive feedback on the terminal display.

If it is determined to induce relearning since the first response data value exceeds the first reference data value, the hospital server stores the first response data value in the patient DB and updates information in the patient DB, the arithmetic process unit redetermines a treatment type based on the updated information in the patient DB, the management server extraction unit extracts an instruction value according to the redetermined treatment type from a management server DB, the terminal extraction unit extracts treatment tool information and virtual treatment simulation information from the waiting room program library based on the instruction value according to the redetermined treatment type, and the terminal output unit outputs the treatment tool information and virtual treatment simulation information on the terminal display.

The first response data value is based on input of a patient in response to a displayed virtual treatment simulation.

The arithmetic process unit sets the first reference data value based on the mean value of first response data values of patients.

The treatment room server determination unit determines, based on a signal value from a head sensor, whether to give negative feedback or give treatment behavior inducing information.

If it is determined to be treatment noncompliance based on a signal value from a head sensor, the treatment room server extraction unit extracts negative feedback information from the treatment room program library, and the treatment room server output unit outputs the extracted negative feedback on the treatment room display.

If it is determined to be treatment compliance based on a signal value from a head sensor, the treatment room server extraction unit extracts treatment behavior inducing information from the treatment room program library, and the treatment room server output unit outputs the extracted treatment behavior inducing information on the treatment room display.

If a treatment initiation signal is received from a controller in response to the treatment behavior inducing information, the treatment room server extraction unit extracts treatment initiation guide information from the treatment room program library, and the treatment room server output unit outputs the extracted treatment initiation guide information on the treatment room display.

Preferably, the information about a treatment situation is in the form of a game using characters.

If it is determined to give positive feedback information since the second response data value is greater than or equal to the second reference data value, the treatment room server extraction unit extracts positive feedback from the treatment room program library, and the treatment room server output unit outputs the extracted positive feedback on the treatment room display.

If it is determined to give negative feedback information since the second response data value is less than the second reference data value, the treatment room server extraction unit extracts negative feedback from the treatment room program library, and the treatment room server output unit outputs the extracted negative feedback on the treatment room display.

The second response data value is based on input of the patient in response to the treatment situation information, and the input is input from a controller.

The second response data value comprises a heart rate data value and a tension data value of the patient received from the controller.

The second response data value is stored in the patient DB.

The arithmetic process unit sets a second reference data value based on the mean value of second response data values of patients.

To achieve the above object, a method for providing customized treatment information for behavioral control of dental patients in accordance with the the invention comprises the steps: in which a management server determines a treatment type of a patient based on information in a patient DB; in which the management server extracts an instruction value according to the determined treatment type from a management server DB; in which a hospital server receives the extracted instruction value from the management server; in which based on the instruction value a waiting room terminal extracts treatment tool information and virtual treatment simulation information from a waiting room program library; in which the waiting room terminal outputs the extracted treatment tool information and virtual treatment simulation information on a terminal display; in which the waiting room terminal compares a first response data value of the patient to the virtual treatment simulation information with a first reference data value and determines whether to give positive feedback or induce relearning; in which based on a signal value from a contact sensor of a treatment tool, a treatment room server extracts relevant treatment tool information and information about a treatment situation in which the treatment tool is used, from a treatment room program library; in which the treatment room server outputs the extracted relevant treatment tool information and information about a treatment situation in which the treatment tool is used, on a treatment room display; and in which the treatment room server compares a second response data value of the patient to the information about a treatment situation with a second reference data value and determines whether to give positive feedback or give negative feedback.

Preferably, the patient DB comprises: a personal information DB comprising names, sexes, and ages; a treatment list DB comprising diagnosis information and teeth positional information; a peculiar aspect DB comprising a treatment compliance level; and a waiting time DB comprising a patient who is waiting, a patient whose medical treatment has been initiated, and a patient whose medical treatment has been finished, and estimated time of waiting.

The treatment type of a patient is determined based on diagnosis information, teeth positional information, and a treatment compliance level.

If it is determined to give positive feedback information since the first response data value is less than or equal to the first reference data value, the method further comprises the steps: in which the waiting room terminal extracts positive feedback from the waiting room program library; and in which the waiting room terminal outputs the extracted positive feedback on the terminal display.

If it is determined to induce relearning since the first response data value exceeds the first reference data value, the method further comprises the steps: in which the hospital server stores the first response data value in the patient DB and updates information in the patient DB; in which the management server redetermines a treatment type based on the updated information in the patient DB; in which the management server extracts an instruction value according to the redetermined treatment type from a management server DB; in which the waiting room terminal extracts treatment tool information and virtual treatment simulation information from the waiting room program library based on the instruction value according to the redetermined treatment type; and in which the waiting room terminal outputs the treatment tool information and the virtual treatment simulation information on the terminal display.

The first response data value is based on input of the patient in response to a displayed virtual treatment simulation.

The method further comprises the step of setting the first reference data value based on the mean value of first response data values of patients.

The method further comprises the step of determining based on a signal value from a head sensor whether to give negative feedback or give treatment behavior inducing information.

If it is determined to be treatment noncompliance based on a signal value from a head sensor, the method further comprises the steps of: extracting negative feedback information from the treatment room program library; and outputting the extracted negative feedback on the treatment room display.

If it is determined to be treatment compliance based on a signal value from a head sensor, the method further comprises the steps of: extracting treatment behavior inducing information from the treatment room program library; and outputting the extracted treatment behavior inducing information on the treatment room display.

If a treatment initiation signal is received from a controller in response to the treatment behavior inducing information, the method further comprises the steps of: extracting treatment initiation guide information from the treatment room program library; and outputting the extracted treatment behavior guide information on the treatment room display.

Preferably, the information about a treatment situation is in the form of a game using characters.

If it is determined to give positive feedback information since the second response data value is greater than or equal to the second reference data value, the method further comprises the steps of: extracting positive feedback from the treatment room program library; and outputting the extracted positive feedback on the treatment room display.

If it is determined to give negative feedback information since the second response data value is less than the second reference data value, the method further comprises the steps of: extracting negative feedback from the treatment room program library; and outputting the extracted negative feedback on the treatment room display.

The second response data value is based on input of the patient in response to the treatment situation information, and the input is input from the controller.

The second response data value comprises a heart rate data value and a tension data value of the patient received from the controller.

The second response data value is stored in the patient DB.

The method further comprises the step of setting the second reference data value based on the mean value of second response data values of patients.

Advantageous Effects of Invention

As stated above, a system and method for providing customized treatment information for behavioral control of dental patients in accordance with the invention is effective in improving the positive understanding of treatment and voluntary participation in treatment by providing animated screens on which characters appear in accordance with the treatment type of a patient and the patient's behavior in response to the treatment.

BRIEF DESCRIPTION OF DRAWINGS

FIG. 1 is an embodiment of a system for providing customized treatment information for behavioral control of dental patients in accordance with the invention.

FIG. 2 is a block diagram depicting in detail the respective elements of the system of FIG. 1.

FIG. 3 is a flowchart of the waiting room stage in a method for providing customized treatment information for behavioral control of dental patients in accordance with the invention.

FIG. 4 is a flowchart of the treatment room stage in a method for providing customized treatment information for behavioral control of dental patients in accordance with the invention.

FIG. 5 is a screen of a waiting room terminal on which treatment tool information is displayed.

FIG. 6 is a screen of a waiting room terminal on which virtual treatment simulation information is displayed.

FIG. 7 is a screen of a treatment room display on which treatment tool information is displayed.

FIG. 8 is a screen of a treatment room display on which information about a treatment situation is displayed.

DESCRIPTION OF EMBODIMENTS

While the present invention is examined in more detail through the embodiments below, the following embodiments do not delimit the scope of the invention.

FIG. 1 is an embodiment of a system for providing customized treatment information for behavioral control of dental patients in accordance with the invention. FIG. 2 is a block diagram depicting in detail the respective elements of the system of FIG. 1.

Referring to FIGS. 1 and 2, a management server 100, a hospital server 200, a waiting room terminal 300, a treatment room server 400, a treatment room display 500, a treatment tool 600, a controller 700, and a treatment chair 800 are connected through wired-wireless networks 10.

The management server 100 comprises an arithmetic process unit 110 which determines a treatment type of a patient based on information in a patient DB 220, a management server extraction unit 120 which extracts an instruction value according to the determined treatment type from a management server DB 130, a management server transmission/reception unit 140 which transmits the extracted instruction value to the hospital server 200 and receives fixed information from the hospital server 200, and a service subscriber identification unit 150 which identifies whether a user accessing the management server 100 is a subscriber.

The management server DB 130 comprises a basic program DB, a waiting room program DB, and a treatment room program DB. In the basic program DB stored are emotional response (happiness, sadness, fear) and feedback (praise, warning). In the waiting room program DB stored are treatment tools, a treatment video, and a treatment audio system which are associated with the waiting room. In the treatment room program DB stored are treatment tools, a treatment video, and a treatment audio system which are associated with the treatment room. In the embodiments the management server DB 130 is included in the management server 100 but the management server DB 130 does not necessarily have to be included in the management server 100.

The hospital sever 200 comprises a hospital server transmission/reception unit 210 which receives the extracted instruction value from the management server 100 and transmits the same to the waiting room terminal 300, a patient DB 220, a hospital server extraction unit 230 which extracts predetermined information about the patient from the patient DB 220, and a hospital server update unit 240 which updates information in the patient DB 220.

The patient DB 220 comprises: a person information DB comprising names, sexes, and ages; a treatment list DB comprising diagnosis information and teeth positional information; a peculiar aspect DB comprising a treatment compliance level; and a waiting time DB comprising a patient who is waiting, a patient whose medical treatment has been initiated, and a patient whose medical treatment has been finished, and estimated time of waiting. In the embodiments, the patient DB 220 is included in the hospital server 200 but the patient DB 220 does not necessarily have to be included in the hospital server 200.

The waiting room terminal 300 comprises a terminal extraction unit 320 which extracts treatment tool information and virtual treatment simulation information from a waiting room program library 310 based on the instruction value received from the hospital server 200, a terminal output unit 340 which outputs the extracted treatment tool information and virtual treatment simulation information on a terminal display 330, a terminal determination unit 350 which compares a first response data value of the patient to the virtual treatment simulation information with a first reference data value and determines whether to give positive feedback or induce relearning, and a terminal transmission/reception unit 360 which receives the instruction value and the first response data value and which transmits the first response data value to the hospital server 200.

In the waiting room program library 310 stored are treatment tools, a treatment video, and a treatment audio system which are associated with the waiting room. When information is collected or a program is updated, the waiting room terminal 300 connects to the management server 100 through the hospital server 200 and references the waiting room program DB in the management server DB 130.

The treatment room server 400 comprises: a treatment room server extraction unit 420 which extracts, based on a signal value from a contact sensor of a treatment tool 600, relevant treatment tool information and information about a treatment situation in which the treatment tool is used, from a treatment room program library 410; a treatment room server output unit 430 which outputs the extracted relevant treatment tool information and information about a treatment situation in which the treatment tool is used, on the treatment room display 500; a treatment room server determination unit 440 which compares a second response data value of the patient to the information about a treatment situation with a second reference data value and determines whether to give positive feedback or give negative feedback; and a treatment room server transmission/reception unit 450 which receives a treatment tool signal value and the second response data value and which transmits the second response data value to the hospital server 200.

In the treatment room program library 410 stored are treatment tools, a treatment video, and a treatment audio system which are associated with the treatment room. When information is collected or programs are updated, the treatment room server 400 connects to the management server 100 through the hospital server 200 and references the treatment room program DB in the management server DB 130.

FIGS. 3 and 4 depict flowcharts of a method for providing customized treatment information for behavioral control of dental patients in accordance with the invention. The method for providing customized treatment information for behavioral control of dental patients is divided largely into the waiting room stage (S100) and the treatment room stage (S200).

FIG. 3 depicts a flowchart of the waiting room stage (S100) and FIG. 4 depicts a flowchart of the treatment room stage (S200).

Referring to FIG. 3, when information about a patient is received, the hospital server extraction unit 230 extracts the relevant patient's diagnosis information, teeth positional information, treatment compliance level, and estimated waiting time information from the patient DB 220, and the hospital server transmission/reception unit 210 transmits the extracted information to the management server 100 (S110).

The arithmetic process unit 110 of the management server 100 determines a treatment type of the relevant patient based on the patient's diagnosis information, teeth positional information, and treatment compliance level (S120).

Determining a treatment type is illustrated below, for example:

X is chosen from X-Y-Z based on diagnosis information (A: the cavity treatment, B: teeth scaling, C: extraction of teeth, etc.). Y is chosen from X-Y-Z based on teeth positional information (a: maxillary, b: mandibular, c: occlusal, etc.). Z is chosen from X-Y-Z based on a treatment compliance level. The treatment compliance level is classified into a': a first compliance level (10-15 points), b': a second compliance level (5-10 points), and c': a third compliance level (less than 5 points). It is determined based on collected behavioral data what compliance level the relevant patient (e.g., a pediatric patient) achieves. There are a total of five items for behavioral data collection: 5 points for attacking, 4 points for yelling, 3 points for crying, 2 points for escaping, and 1 point for covering the mouth. A maximum of 15 points may be given by overlapping points depending on treatment compliance behavior of the patient.

Once a treatment type is determined based on the chosen X, Y, and Z, the time for and amount of information to be given for the patient is determined in consideration of estimated time of waiting. The time during which information is given varies depending on the estimated time of waiting. For instance, assuming that the basic time required is 5 minutes, if estimated time of waiting is less than 5 minutes, only the essential information is given (the essential information means a program that has been reset to less than about 2 minutes by providing the treatment tool information in the virtual treatment simulation without separately providing the treatment tool information.). If estimated time of waiting is 5 minutes or more, initiation time is controlled at which a pediatric patient is provided with treatment tool information and virtual treatment simulation information. In other words, information is provided at a time when the estimated waiting time taken to move from a waiting room to the treatment room is expected to be 5 minutes by the provided basic time of 5 minutes so that treatment can be initiated immediately when the provided information ends.

The management server extraction unit 120 extracts an instruction value according to a treatment type from the management server DB 130, and the management server transmission/reception unit 140 transmits the extracted instruction value to the hospital server 200 (S130).

The hospital server transmission/reception unit 210 transmits the instruction value again to the waiting room terminal 300 (S140).

The terminal extraction unit 320 extracts treatment tool information and virtual treatment simulation information according to the instruction value from the waiting room program library 310, and the terminal output unit 340 outputs the treatment tool information and the virtual treatment simulation information on the terminal display 330 (S150).

The treatment tool information helps the patient learn in advance a tool used to treat himself or herself, thereby changing a negative image of a treatment tool to a familiar image. FIG. 5 is a screen of the waiting room terminal on which treatment tool information is displayed. The patient, while looking at a treatment tool used for the treatment of himself or herself, is provided with the purpose of relevant treatment tool and sensory information perceived when the tool is used.

The virtual treatment simulation information is provided information by integrating the procedural information and the sensory information while the patient becomes a dentist in virtual reality and treats in person a character who receives the same treatment as treatment to be given himself or herself in reality under conditions of the increased familiarity with the treatment tool. FIG. 6 is a screen of the waiting room terminal on which the virtual treatment simulation information is displayed. Through the virtual treatment simulation information, the patient naturally learns how to use a treatment tool, a method and procedure for treatment, and the appearance changed after treatment, thereby increasing a motivation for treatment.

The terminal determination unit 350 compares a first response data value of the patient to the virtual treatment simulation information with a first reference data value and determines whether to give positive feedback or induce relearning (S160).

The first response data value is based on input of the patient in response to a displayed virtual treatment simulation, and means the time taken for the patient to start with and end a virtual treatment simulation. For example, assuming that it took a total of 4 minutes for the patient to start with and end a virtual treatment simulation and assuming that a first reference data value is 3 minutes, if a first response data value of the relevant patient is compared with the first reference data value, the patient is classified as Group b and relearns (a: a group taking time shorter than or equal to a first reference data value, b: a group taking time longer than a first reference data value).

The first response data value is transmitted to the hospital server 200 through the terminal transmission/reception unit 360 and stored in the patient DB 220.

The first reference data value means the mean value of response data values of patients. The first reference data value is stored in the management server DB 130, and transmitted together with an instruction value according to a treatment type of the patient to the waiting room terminal 300 through the hospital server 200.

If it is determined to give positive feedback since the first response data value is less than or equal to the first reference data value, the terminal extraction unit 320 extracts positive feedback from the waiting room program library 310, and the terminal output unit 340 outputs the extracted positive feedback on the terminal display 330 (S170a).

An example of positive feedback can be a screen on which a character appears and says "Good job", "Shall we move to a treatment room?" and so on.

If it is determined to induce relearning since the first response data value exceeds the first reference data value, the hospital server update unit 260 stores the first response data value transmitted from the terminal transmission/reception unit 360 in the patient DB 220, specifically in the peculiar aspect DB, and updates information in the patient DB 220. The hospital server extraction server 230 extracts the relevant patient's diagnosis information, teeth positional information, treatment compliance level, and estimated time of waiting from the updated patient DB, and the hospital server transmission/reception unit 210 transmits the extracted information to the management server 100 (S172b).

The arithmetic process unit 110 of the management server 100 redetermines a treatment type of the patient based on the patient's diagnosis information, teeth positional information, and treatment compliance level (S174b). At this time, the first reference data value which is the mean value of response data values of patients is also changed by the arithmetic process unit 110. For instance, assuming that a first reference data value is 3 minutes, if it took a total of 2 minutes for patient A to start with and end a virtual treatment simulation in the waiting room, the time required of patient A is delivered to the management server DB 130 through the hospital server 200. So, if next patient B uses the program (virtual treatment simulation information), the first reference data value is adjusted to 2 minutes 45 seconds such that a first response data value of patient B is compared with the adjusted first reference data value.

When a treatment type is redetermined, the management server extraction unit 120 extracts an instruction value according the treatment type from the management server DB 130, and the management server transmission/reception 140 transmits the extracted instruction value and the changed first reference data value to the hospital server 200 (S176b).

The hospital server transmission/reception unit 210 transmits the instruction value and the changed first reference data value again to the waiting room terminal 300 (S178b).

The terminal extraction unit 320 extracts treatment tool information and virtual treatment simulation information according to the instruction value from the waiting room program library 310, and the terminal output unit 340 outputs the treatment tool information and the virtual treatment simulation information on the terminal display 330 (S180b).

The terminal determination unit 350 compares a first response data value of the patient to the virtual treatment simulation information with the changed first reference data value and determines whether to give positive feedback or induce relearning (S182). Until before it is determined to give positive feedback, a series of procedures associated with inducing relearning as explained earlier is repeated.

When the procedure in the waiting room is completed, the patient moves to the treatment room, and the treatment room stage (S200) begins.

When the patient lies down on the treatment chair 800 in the treatment room, based on a signal value from a head sensor of the treatment chair 800, the treatment room server determination unit 440 determines whether to give negative feedback or give treatment behavior inducing information (S210). For example, if the head of the patient is not in contact with the head sensor, it is determined to be treatment non-compliance since a value of the head sensor is sensed as an off-state. If the head of the patient is in contact with the head sensor, it is determined to be treatment compliance since a value of the head sensor is sensed as an on-state.

If it is determined to be treatment non-compliance based on the signal value from the head sensor of the treatment chair 800, the treatment room server extraction unit 420 extracts negative feedback information from the treatment room program library 410, and the treatment server output unit 430 outputs the extracted negative feedback on the treatment room display 500 (S220a). An example of negative feedback information can be a screen on which a character appears and says "Lie down and stay" and so on. Also, when the patient moves his or her head during treatment or there are body movements to refuse treatment, negative feed can be output.

If it is determined to be treatment compliance based on a signal value from the head sensor, the treatment room server extraction unit 420 extracts treatment behavior inducing information from the treatment room program library 410, and the treatment room server output unit 430 outputs the extracted treatment behavior inducing information on the treatment room display 500 (S220b). An example of treatment behavior inducing information can be a screen on which a character appears and says "Let's begin the treatment", "Push the treatment initiation button of the controller" and so on.

When a treatment initiation signal is received from a controller 700 in response to the treatment behavior inducing information, the treatment room server extraction unit 420 extracts treatment initiation guide information from the treatment room program library 410, and the treatment room server output unit 430 outputs the extracted treatment initiation guide information on the treatment room display 500 (S230). An example of treatment initiation guide information can be a screen on which a character appears and says "Let's open your mouth" and so on. The controller 700 is a control terminal manipulated by the patient.

When treatment is initiated, based on a signal value from a contact sensor of the treatment tool 600, the treatment room server extraction unit 420 extracts relevant treatment tool information and information about a treatment situation in which the treatment tool is used, from the treatment room program library 410, and the treatment room server output unit 430 outputs the extracted relevant treatment tool information and information about a treatment situation in which the treatment tool is used, on the treatment room display 500 (S240).

For example, in case of the cavity treatment, when a treatment tool for the the cavity treatment is out of a position in which the treatment tool should be stored, the treatment room server 400 senses whether the signal value of a contact sensor of the treatment tool 600 is on/off.

The treatment room server extraction unit 420 extracts, according to the signal value, treatment tool information and information about a treatment situation in which the treatment tool is used, from the treatment room program library 410. For instance, in case of the cavity treatment, on the treatment room display (e.g., a ceiling mounted monitor) provided is about 5-minute-information in the form of an animation about a treatment tool actually used for the patient and about the characteristics of the treatment tool. For example, if a dentist uses an actual dental drill, the treatment room display provides an animated dental drill and sensory information perceived when the dental drill is used, and if a treatment tool for use is changed, information about a new treatment tool to be used is provided by sensing of the contact sensor. FIG. 7 depicts a screen of treatment tool information.

The information about a treatment situation in which the treatment tool is used is animated information about a situation where a character carrying a treatment tool used for treatment appears and beats a cavity man. While the information about a treatment situation is provided, the patient manipulates the controller so that the character beats the cavity man. FIG. 8 depicts a screen of the treatment room display on which the information about a treatment situation is displayed.

The treatment room server determination unit 440 compares a second response data value of the patient to the information about a treatment situation with a second reference data value and determines whether to give positive feedback or give negative feedback (S250).

The second response data value can be input of the patient in response to the information about a treatment situation. For instance, in case of the cavity treatment, on the treatment room display 500 displayed is the game type information about a treatment situation in which a specific character fights with a cavity germ. The patient manipulates the controller 700 so that the character beats the cavity germ. In this case, if a treatment tool used for the patient is changed, a treatment tool used by the character is likewise changed.

A second response data value is, for example, collection of data from the controller 700 about whether or not a pediatric patient makes a response per second when sections are set at 30-second intervals, specifically meaning the number of responses made for 30 seconds (A second response data value of a pediatric patient having made a response every second is calculated as 30 times and, if a second reference data value is 15 times, is greater than or equal to the reference data value. Therefore, the pediatric patient is given positive feedback).

A second reference data value means the mean value of second response data values of patients.

The terminal transmission/reception unit 360 transmits the second response data value of the patient to the hospital server 200. The hospital server update unit 240 stores the transmitted second response data value in the patient DB 220 and updates information in the patient DB 220. The second reference data value is set based on the updated information in the patient DB.

In other words, an average value of the number of responses made by pediatric patient A per section in the treatment room is delivered to the patient DB and used to enable the arithmetic process unit of the management server to set a new second reference data value. For instance, a second reference data value is 16 times for 30 seconds and the mean of second response data values of pediatric patient A is 10 times for 30 seconds, a newly adjusted second reference data value becomes 13 times for 30 seconds.

The second response data value may be biodata comprising a heart rate data value and a tension data value of the patient received from the controller 700. The heart rate and tension signal of the patient is collected through a contact sensor and a pressure sensor of the controller 700. The collected heart rate (normal/abnormal) and tension (high/low) values are compared with the second reference data value to determine whether to give positive feedback or give negative feedback.

Such biodata is second response data about the patient and the terminal transmission/reception unit 360 transmits the second response data value of the patient to the hospital server 200. The hospital server update unit 240 stores the transmitted second response data value in the patient DB 220 and updates information in the patient DB 220.

If it is determined to give positive feedback information since the second response data value is greater than or equal to the second reference data value, the treatment room server extraction unit 420 extracts positive feedback from the treatment room program library 410, and the treatment room server output unit 430 outputs the extracted positive feedback on the treatment room display 500 (S260a). An example of positive feedback information can be a screen on which a character appears and says "You are doing well" and so on.

If it is determined to give negative feedback information since the second response data value is less than the second reference data value, the treatment room server extraction unit 420 extracts negative feedback from the treatment room program library 410, and the treatment room server output unit 430 outputs the extracted negative feedback on the treatment room display 500 (S260b). An example of negative feedback information can be a screen on which a character appears and says "Shall we try a little more?", "Don't be nervous", "Don't be afraid" and so on.

As above, according to the present invention, an animated screen on which a character appears is appropriately given depending on a treatment type of a patient and treatment response behavior of the patient, thereby providing the effect of increasing positive understanding of treatment and voluntary participation in treatment.

Although the preferred specific embodiments of the invention have been explained above, the invention is not limited to any specific embodiment stated above and any person skilled in the art to which the invention pertains can implement various modifications without departing from the substance of the invention claimed in the claim scope thereof, as well as such modifications fall within the scope of the description of the claims.

REFERENCE SIGNS LIST

100: Management server
110: Arithmetic process unit
120: Management server extraction unit
130: Management server DB 140: Management server transmission/reception unit
150: Service subscriber identification unit
200: Hospital server
210: Hospital server transmission/reception unit
220: Patient DB
230: Hospital server extraction unit
240: Hospital server update unit
300: Waiting room terminal
320: Terminal extraction unit
330: Terminal display
340: Terminal output unit
350: Terminal determination unit
360: Terminal transmission/reception unit
400: Treatment room server
420: Treatment room server extraction unit
430: Treatment room server output unit
440: Treatment room server determination unit
450: Treatment room server transmission/reception unit
500: Treatment room display
600: Treatment tool
700: Controller
800: Treatment chair

What is claimed is:

1. A method for providing customized treatment information, the method comprising the steps of:
    determining a treatment type of a patient based on information in a patient database (DB), the information in the patient DB including a point system based on a treatment compliance level;
    extracting an instruction value according to the determined treatment type from a management server DB;
    receiving the extracted instruction value from the management server;
    based on the instruction value, extracting treatment tool information and virtual treatment simulation information from a waiting room program library;
    outputting the extracted treatment tool information and virtual treatment simulation information on a terminal display;
    comparing a first response data value of the patient to the virtual treatment simulation information with a first reference data value and determining whether to give positive feedback or induce relearning;
    based on a signal value from a contact sensor of a treatment tool, extracting relevant treatment tool information and information about a treatment situation in which the treatment tool is used from a treatment room program library;
    outputting the extracted relevant treatment tool information and information about a treatment situation in which the treatment tool is used on a treatment room display;
    comparing a second response data value of the patient to the information about a treatment situation with a second reference data value and determining whether to give positive feedback or first negative feedback with respect to the treatment situation;
    determining a treatment compliance or non-compliance based on a signal value from a head sensor; and
    providing second negative feedback in response to treatment non-compliance and inducing treatment initiation in response to treatment compliance via the treatment room display.

2. The method as defined in claim 1, wherein the patient DB comprises:
    a personal information DB comprising names, sexes, and ages;
    a treatment list DB comprising diagnosis information and tooth position information;
    a peculiar aspect DB comprising the treatment compliance level; and
    a waiting time DB comprising a patient who is waiting, a patient whose medical treatment has been initiated, and a patient whose medical treatment has been finished, and estimated time of waiting.

3. The method as defined in claim 2, wherein the treatment type of the patient is further determined based on the tooth position information.

4. The method as defined in claim 1, wherein if it is determined to give positive feedback since the first response data value is less than or equal to the first reference data value, the method further comprises the steps of:
    extracting positive feedback from the waiting room program library; and
    outputting the extracted positive feedback on the terminal display.

5. The method as defined in claim 1, wherein if it is determined to induce relearning since the first response data value exceeds the first reference data value, the method further comprises the steps of:
    storing the first response data value in the patient DB and updating information in the patient DB;
    determining a redetermined treatment type based on the updated information in the patient DB;
    extracting a second instruction value according to the redetermined treatment type from the management server DB;
    based on the second instruction value according to the redetermined treatment type, extracting treatment tool information and virtual treatment simulation information from the waiting room program library; and
    outputting the treatment tool information and virtual treatment simulation information on the terminal display.

6. The method as defined in claim 1, wherein the first response data value is based on input of the patient in response to a displayed virtual treatment simulation.

7. The method as defined in claim 1, further comprising the step of setting the first reference data value based on a mean value of first response data values of patients.

8. The method as defined in claim 1, wherein if it is determined to be treatment noncompliance based on the signal value from the head sensor, the method further comprises the steps of:
    extracting the second negative feedback information from the treatment program library; and
    outputting the extracted second negative feedback on the treatment room display.

9. The method as defined in claim 1, wherein if it is determined to be treatment compliance based on the signal value from the head sensor, the method further comprises the steps of:
    extracting treatment initiation inducing information from the treatment room program library; and
    outputting the extracted treatment initiation inducing information on the treatment room display.

10. The method as defined in claim 9, wherein if a treatment initiation signal is received from a controller in response to the treatment initiation inducing information, the method further comprises the steps of:
    extracting treatment initiation guide information from the treatment room program library; and
    outputting the extracted treatment initiation guide information on the treatment room display.

11. The method as defined in claim 1, wherein the information about a treatment situation is in the form of a game using characters.

12. The method as defined in claim 1, wherein if it is determined to give positive feedback since the second response data value is greater than or equal to the second reference data value, the method further comprises the steps of:
    extracting positive feedback from the treatment room program library; and
    outputting the extracted positive feedback on the treatment room display.

13. The method as defined in claim 1, wherein if it is determined to give first negative feedback information since the second response data value is less than the second reference data value, the method further comprises the steps of:
    extracting the first negative feedback from the treatment room program library; and
    outputting the extracted first negative feedback on the treatment room display.

14. The method as defined in claim 1, wherein the second response data value is based on input of the patient in response to treatment situation information, and the input is input from a controller.

15. The method as defined in claim 1, wherein the second response data value comprises a heart rate data value and a tension data value of the patient received from a controller.

16. The method as defined in claim 1, wherein the second response data value is stored in the patient DB.

17. The method as defined in claim 1, further comprising the step of setting the second reference data value based on a mean value of second response data values of patients.

* * * * *